United States Patent [19]

Okonogi et al.

[11] Patent Number: 4,588,595

[45] Date of Patent: May 13, 1986

[54] CULTURE CONTAINING A VIABLE CELL MASS OF BIFIDOBACTERIA AND LACTIC ACID BACTERIA

[75] Inventors: Shigeo Okonogi, Tokyo; Takuji Kawashima, Kawasaki; Tsutomu Kudo, Yokohama; Hiroya Yuguchi, Tokyo; Akinori Hiramatsu, Hachioji; Susumu Teraguchi, Tama; Tomoko Yaeshima, Tokyo, all of Japan

[73] Assignee: Morinaga Milk Industry Co., Ltd., Tokyo, Japan

[21] Appl. No.: 547,827

[22] Filed: Nov. 2, 1983

[30] Foreign Application Priority Data

Nov. 9, 1982 [JP] Japan .................. 57-195376

[51] Int. Cl.$^4$ ............ A23C 9/127; A23C 23/00; C12N 1/20
[52] U.S. Cl. ........................ 426/43; 426/61; 435/253; 435/885
[58] Field of Search ............ 426/43, 61; 435/253, 435/885

[56] References Cited

U.S. PATENT DOCUMENTS

| 4,087,559 | 5/1978 | Mutzi et al. | 426/43 |
| 4,187,321 | 2/1980 | Mutzi et al. | 426/43 |
| 4,298,619 | 11/1981 | Mutzi et al. | 426/43 |
| 4,339,464 | 7/1982 | Vedamuthu | 435/885 X |

FOREIGN PATENT DOCUMENTS

| 1952361 | 4/1971 | Fed. Rep. of Germany | 426/43 |
| 2939528 | 4/1981 | Fed. Rep. of Germany | 426/43 |

Primary Examiner—David M. Naff
Attorney, Agent, or Firm—Jordan and Hamburg

[57] ABSTRACT

A culture containing a viable mass of Bifodobacteria and lactic acid bacteria is obtained by incubating separately or together microorganisms of the genus Bifidobacterium and Lactobacillus, and the species *Streptococcus thermophilus* in a medium containing milk as the main ingredient. The *Streptococcus thermophilus* is a strain having high oxygen uptake. When incubated separately, the microorganisms are mixed together after incubating. In the presence of the high oxygen uptake *Streptococcus thermophilus*, a high survival fraction of the Bifidobacteria is obtained when the culture is stored under aerobic conditions. The culture is useful in preparing food, medicine or feed.

5 Claims, No Drawings

CULTURE CONTAINING A VIABLE CELL MASS OF BIFIDOBACTERIA AND LACTIC ACID BACTERIA

This invention relates to a culture containing viable cells of Bifidobacteria and lactic acid bacteria with less mortality of the Bifidobacteria when stored in aerobic conditions, which comprises a viable cell mass of microorganisms belonging to the genus Bifidobacterium (which will be hereinafter referred to as "Bifidobacteria"), and a viable cell mass of microorganisms belonging to the genus Lactobacillus (which will be hereinafter referred to as "lactobacillus bacteria"), and a new Streptococcus thermophilus having a high oxygen uptake ability (which will be hereinafter referred to as "S bacteria"), and a process for preparing the same.

The Bifidobacteria are the most predominant bacteria in human intestines, and their significance in health has been widely studied. They have been so far utilized in medicines for intestinal disorders, food and nutrients, etc.

The Bifidobacteria also play a favorable role in animal intestines which is similar with the case in human intestines, and have been utilized as animal feed.

However, the Bifidobacteria are incapable of surviving in storage for a prolonged period in an aerobic environment where oxygen exists at a lower pH range because they are obligatory anaerobes and their acid resistivity is very limited. It has not been possible to ensure a considerable number of viable Bifidobacteria cells in cultured products when the Bifidobacteria are applied to them. [Umada: New Food Industry, Volume 24, No. 1, page 63 (1982)]. The value of the survival fraction of Bifidobacteria, in the cultured products is expressed by a percentage of the number of viable cells of Bifidobacteria after being stored to that of viable cells of Bifidobacteria at the moment immediately after the preparation was lowered due to a synergistic adverse effect of exposure to oxygen in the air and to low pH in the process of preparation and storage. To solve the problems described above, (a) a sophisticated manner for manufacturing or a special product form which prevents the product from contact with air during the preparation and storage, and (b) application of a mutant strain of Bifidobacteria having acid and oxygen resistances has been attempted. However, procedure (a) causes in increase in production cost. The acid or oxygen resistant mutants of *Bifidobacterium breve* (Japanese Examined Patent Application Publication Gazette No. 42250/1981; Japanese Unexamined Patent Application Publication Gazette No. 99190/1982), *Bifidobacterium bifidum* (Japanese Examined Patent Application Publication Gazette No. 42250/1981) and *Bifidobacterium longum* (Japanese Patent Application No. 106182/1982, filed by the present inventors) were isolated, but this technology is solely applicable to the restricted species of the Bifidobacteria and is less practical.

The oxygen uptake ability of *Lactobacillus acidophilus, Lactobacillus arabinosus, Lactobacillus batatas, Lactobacillus casei, Lactobacillus delbrueckii, Lactobacillus fermentii, Lactobacillus plantarium* and *Lactobacillus sake*, belonging to the genus Lactobacillus, have been reported [Kitahara and Fukui: Journal of the Agricultural Chemical Society of Japan, Volume 26, page 555 (1952); C. F. Strittmatter: Journal of Biological Chemistry, Volume 234, page 2789 (1959); M. I. Dolin: The Bacteria, Ed. I. C. Gunsalus, R. Y. Stainer, Acad. Press Inc., page 425 (1961); Iwamoto et al: Journal of the Pharmaceutical Society of Japan, Volume 99, page 354 (1979)], *Leuconostoc mesenteroides* belonging to the genus Leuconostoc [Iwamoto et al: Journal of the Pharmaceutical Society of Japan, Volume 99, page 354 (1979)], and *Streptococcus agalactiae, Streptococcus cremoris, Streptococcus faecalis, Streptococcus faecium, Streptococcus lactis, Streptococcus liquefaciens* and *Streptococcus mastitidis*, belonging to the genus Streptococcus [O. J. O Kane, I. C. Gunsalus: Journal of Bacteriology, Volume 56, page 499 (1948); Obayashi et al: Journal of the Agricultural Chemical Society of Japan, Volume 34, page 272 (1960); M. I. Dolin: Bacteria, Ed. I. C. Gunsalus & R. Y. Stainer, Acad. Press Inc., page 425 (1961); M. N. Mickelson: Journal of Bacteriology, Volume 94, page 184 (1967); R. F. Anders et al: Applied Microbiology, Volume 19, page 608 (1970); M. J. Coventry: The Australian Journal of Dairy Technology, Volume 33, page 148 (1978); Iwamoto et al: Journal of the Pharmaceutical Society of Japan, Volume 99, page 354 (1979)]. Tinson et al. reported that the oxygen uptake rate of *Streptococcus thermophilus* (which will be hereinafter referred to as "thermophilus bacteria") was 7.3 $\mu$moles for 90 minutes per 12 mg of dried cell mass at 33.5° C. when skim milk containing 0.1% yeast extract is used as a substrate [The Australian Journal of Dairy Technology, Volume 37, page 14 (1982)]. This oxygen uptake ability, when converted to units of in one minute per one mg of dried cell mass, was 6.76 nano moles of oxygen molecules. The oxygen uptake ability will be hereinafter expressed by nano moles as defined above. These past studies prompted the present inventors to examine the stimulation of viability of Bifidobacteria by removal of oxygen from the environment which might be achieved by the oxygen uptake ability of coexistent Streptococcus or lactobacillus bacteria.

The ratio of the cell number of lactobacillus bacteria to that of thermophilus bacteria in conventional fermented milk is in a range of approximately 1:4–4:1 [R. K. Robinson, A. Y. Tamime: Journal of the Society of Dairy Technology, Volume 28, page 149 (1975); Morichi: Bulletin of Japan Dairy Technical Association, Volume 25, page 2 (1975); Kikuchi: Fermentation and Industry, Volume 37, page 133 (1979)]. Schüler et al. [Milchwissenschaft, Volume 23, No. 9, page 554 and No. 10, page 614 (1968)] described a starter composition for fermented milk of 5:1:1 approximately in the ratio of Streptococcus:*Lactobacillus acidophilus*:Bifidobacteria, and observed that the composition of the three microorgaimsms for the starter in the resulting fermented product was 15:1:2 after the fermentation was terminated. The survival fraction of the Bifidobacteria was about 1% when the fermented milk was preserved at a pH of 4.6–4.9 for 7 days.

As described above, the survival fraction of the Bifidobacteria were considerably lowered in the presence of lactobacillus and thermophilus bacteria which seemed to be due to a limited oxygen uptake ability of the latter two bacteria.

However, the present inventors isolated the S bacteria, a new strain of thermophilus bacteria, which have a high oxygen uptake ability. The survival fraction of the Bifidobacteria in fermented milk, having a low pH, was remarkably elevated in the presence of the said S bacteria owing to lowering the oxygen concentration in the environment.

An object of the present invention is to provide a culture which causes a high survival fraction of the Bifidobacteria when the culture is stored under aerobic conditions and also a process for preparing the same.

Another object of the present invention is to provide a culture which is to be utilized for food, as a nutrient, medicines for intestinal disorders and animal feed having a high survival fraction of the Bifidobacteria even when the culture is stored under aerobic conditions.

The details of the present invention will be described below:

A culture according to the present invention contains at least known Bifidobacteria and lactobacillus bacteria, and the novel S bacteria, in which the number of viable cells of the S bacteria in a culture immediately after preparation is at least 10 times as many as that of the lactobacillus bacteria. According to the procedure of the present invention, the number of viable cells of the Bifidobacteria in one gram of a culture immediately after preparation is at least $2 \times 10^7$, and the survival fraction of the Bifidobacteria when stored at 5° C. for 7 days or equivalent conditions, is assured to be at least 5%. The total number of viable cells of Bifidobacteria in one gram of a culture immediately after preparation is at least $1.3 \times 10^8$.

This remarkable effect for prevention of the Bifidobacteria from mortality in a culture according to the present invention is due to a high oxygen uptake ability of the S bacteria contained therein, and such a distinguished survival of the Bifidobacteria has not heretofore been possible. Thus, a culture according to the present invention can be utilized for food, as a nutrient or as an animal feed as such or after being subjected to conventional processing, or can be utilized for medicines for intestinal disorders after freeze-drying of the culture according to conventional procedures.

The process for preparing a culture according to the present invention is as follows:

A culturing medium for the present invention contains cow's milk, skim milk, reconstituted skim milk or their concentrates as the main ingredient with or without the addition of growth-promoting substances for the individual bacteria which have been sterilized according to conventional procedures. The sterilized and cooled medium is inoculated with starter cultures of Bifidobacteria, lactobacillus bacteria and S bacteria which is prepared according to conventional procedures in a ratio of 100:0.5–50:3–600 by weight depending on the desired object when the quantity of the Bifidobacteria is taken as 100. The starter mixture is inoculated in the medium at a concentration of 1.4–16% (V/V).

Culturing is conducted at 37°–42° C. for 3–24 hours according to conventional procedures. Immediately after preparation, one gram of the culture thus obtained normally contains $2$–$500 \times 10^7$, $1$–$20 \times 10^8$ and $5$–$100 \times 10^8$ viable cells of the Bifidobacteria, of the S bacteria, and of the lactobacillus bacteria respectively.

Alternatively, subcultures of the Bifidobacteria, the lactobacillus bacteria and the S bacteria are inoculated in the separate media in concentrations of 3–10% (V/V), 1–5% (V/V), and 1–5% (V/V), respectively, and cultured at 37°–42° C. for 3–24 hours to obtain the starter cultures. One gram of the respective starter contains $5$–$50 \times 10^8$ viable cells of the Bifidobacteria, $2$–$20 \times 10^8$ viable cells of the lactobacillus, and $1$–$10 \times 10^8$ viable cells of the S bacteria. Then, the starters of the Bifidobacteria (the quantity is taken as 100), the lactobacillus bacteria and the S bacteria are mixed in a ratio of 100:0.28–625:11–24,800 by weight, depending upon the concerned object, to obtain a mixed culture.

As described above, the process for preparing a culture according to the present invention is very simple and only requires the conventional installation processes, but exhibits an effect of a remarkable increase of the survival fraction of the Bifidobacteria after being stored owing to the function of the novel S bacteria.

(1) Isolation of the strains belonging to Streptococcus thermophilus:

The strains belonging to Streptococcus thermophilus were isolated according to the following method by Ozawa et al [Bulletin of the national Institute of Agricultural Sciences, Series G (Husbandry), No. 5, page 41 (1953)]. Numerous preparations of the coagulated milk which were obtained by allowing raw milk to stand at 45°–50° C. for 4–5 days, or naturally acidified milk was microscopically inspected. Those samples, in which the existences of Streptococcus were confirmed, were inoculated in 10% (W/W) reconstituted skim milk sterilized at 115° C. for 15 minutes in a concentration of 5% (V/V) and cultured at 45°–50° C. Then cultures were transferred 2–3 times in the same manner as above, and one platinum loopful of the cultures were spread onto an agar plate of M-17 medium [Applied Microbiology, Volume 29, No. 6, page 807 (1975)] and incubated at 40° C. for 2–3 days for colony formation. bacteriological properties of the cells of the colonies were compared to those of the thermophilus bacteria described in the said Bergey's Manual of Determinative Bacteriology, and 40 strains identified to be Streptococcus thermophilus.

(2) Oxygen uptake ability of the thermophilus bacteria:

40 strains belonging to the Streptococcus thermophilus which were isolated from coagulated milk and naturally acidified milk, Streptococcus thermophilus 9Y which was donated by Dr. Morichi of National Institute of Animal Industry as an authentic strain [The Japanese Journal of Zootechnical Science, Volume 53, page 161 (1982)] and Streptococcus thermophilus ATCC 19258, which was obtained from American Type Culture Collection and abbreviated as "ATCC" hereinafter, were subjected to determination of the oxygen uptake ability of the following manner.

They were inoculated in a culture medium [Journal of the Agricultural Chemical Society of Japan, Volume 45, page 423 (1971)] in a concentration of 5% (V/V), and subjected to stationary culturing at 37° C. for 16 hours. Cells were separated from the resulting culture medium by centrifugation, and aseptically washed with a sterilized physiological saline. The cells were then suspended in a sterilized physiological saline in a concentration of 3–5 mg of cell mass (dry basis) per ml. The oxygen uptake ability of each strain was determined according to the manometric method by Warburg [Yoshikawa et al: Kagaku no Ryoiki (Journal of Japanese Chemistry) special issue, No. 13, "Warburg's manometer", Nankodo, February (1954)], as outlined below:

A reaction vessel with two side compartments was used. One ml of the said bacterial suspension and 0.5 ml of 0.1M sterilized phosphate buffer solution having a pH of 6.0 were placed in the main compartment of the reaction vessel, and two aliquots of 0.75 ml of 20% (W/W) sterilized reconstituted skim milk was placed in the two side compartments for a substrate solution. A filter paper, impregnated with 0.2 ml of 20% (W/V) potassium hydroxide solution, was placed in an auxiliary compartment as a carbon dioxide absorber. The vessel was shaken for 5 minutes at 37° C. and then the substrate solutions in the side compartments were poured into the bacterial suspension. The oxygen uptake ability was measured at every 3 minutes to determine the maximum uptake rate, which was defined as the oxygen uptake ability.

The oxygen uptake ability by the tested strains is tabulated in Table 1.

TABLE 1

| Strain | oxygen uptake ability in nano moles |
|---|---|
| 9Y | 19.8 |
| ATCC 19258 | 10.1 |
| STH - 01 | 30.0 |
| STH - 17 | 37.3 |
| STH - 23 | 42.3 |
| STH - 50 | 78.5 |
| STH - 15 | 14.7 |
| STH - 32 | 12.1 |
| other 34 strains | less than 18.5 |

As is obvious from Table 1, 36 strains among the isolated 40 strains had an oxygen uptake ability of less than 18.5 nano moles, whereas the oxygen abilities of the other four strains were 30.0–78.5 nano moles. The standard strain, 9Y, and ATCC 19258 strain had an oxygen uptake ability of 19.8 and 10.1 nano moles respectively.

The present inventors attempted to measure the oxygen uptake ability of the four strains, which had a high oxygen uptake ability, according to the same procedure as the method by Tinson et al. However these four strains had such a remarkably high oxygen uptake ability that the measurement after 90 minutes reaction by the method of Tinson et al. was not possible. Thus the time period, required for an uptake of $7.3\mu$ moles of oxygen molecules as described by Tinson et al., was measured according to the same procedure as the method by Tinson et al. The value by Tinson et al. was 90 minutes, whereas those value of strains STH-01 and STH-23, strain STH-17, and of strain STH-50 were 26, 28 and 21 minutes respectively. Those values of strain 9Y and strain ATCC 19258 were 46 and 140 minutes respectively. STH-01, 17, 23 and 50 had the oxygen uptake abilities which were remarkably higher than in the case of the other strains.

(3) Bacteriological properties of STH-01, 17, 23 and 50:

The present inventors studied the bacteriological properties of these four strains and found that the bacteriological properties, other than a high oxygen uptake ability, were identical with those of the authentic thermophilus bacteria described in Bergey's Manual of Determinative Bacteriology as given below:

(A) Form of the cell aerobically incubated at 37° C. for 48 hours on an M-17 agar plate:
 a. Size (diameter): 0.7–0.9 μm
 b. Shape: spherical or ovoid, pair or chain
(B) Form of colonies aerobically cultured at 37° C. for 48 hours on an M-17 agar plate:
 a. Shape: circular
 b. Elevation: convex circle
 c. Periphery: smooth
 d. Size (diameter): 0.5–1.5 mm
 e. Color tone: whitish and opaque
 f. Surface: smooth and lustrous
(C) Gas: non-producing
(D) Does not grow below 20° C.
(F) Non-motile
(G) Endospore not formed.
(H) Gram-positive
(I) Benzidine-negative
(J) Catalase-negative
(K) Survives when heating at 65° C. for 30 minutes.
(L) Does not grow in the presence of 2% (W/V) sodium chloride.
(M) Does not grow in milk containing 0.1% (W/V) methylene blue.
(N) Does not grow at pH 9.6.
(O) Acid is produced from glucose, fructose, sucrose and lactose, no acid is produced from arabinose, xylose, raffinose, maltose, trehalose, inulin, mannitol, sorbitol, salicin and glycerol.
(P) Does not produce ammonia from arginine.

Even after the successive transfer of culture over 20 times, they had a high oxygen uptake ability. Thus, the present inventors classified these microorganisms as novel strains and termed the strains STH-01, STH-17, STH-23 and STH-50 as *Streptococcus thermophilus* M-8202, *Streptococcus thermophilus* M-8203, Streptococcus thermophilus M-8204 and *Streptococcus thermophilus* M-8205 respectively, which were deposited in Fermentation Research Institute, Agency of Industrial Science and Technology on Oct. 22, 1982 with accession numbers of FERM BP-351, FERM BP-352, FERM BP-353 and FERM BP-354 respectively.

(4) Ratio of number of viable cells of the thermophilus bacteria to that of the lactobacillus bacteria:

M-8205 (STH-50) and STH-32, typical strains of the S bacteria and the thermophilus bacteria having a low oxygen uptake ability respectively, the *Lactobacillus bulgaricus* and *Bifidobacterium longum* (ATCC 15708), Bifidobacteria for typical strains of lactobacillus bacteria, were used to prepare a fermented milk product. The ratio of the number of viable cells of the thermophilus bacteria to that of the lactobacillus bacteria was varied in the ferment milk products and the survival of the Bifidobacteria in them were tested. Starters of the thermophilus bacteria and the lactobacillus bacteria for the test were prepared by inoculating subcultures of them separately in 10% (W/W) reconstituted skim milk which was sterilized at 115° C. for 15 minutes each in a concentration of 3% (V/V), followed by culturing at 37° C. for 16 hours. A starter of the Bifidobacteria was prepared by inoculating the subculture of it in 15% (W/W) reconstituted skim milk containing 0.25% (W/W) yeast extract which was sterilized at 115° C. for 15 minutes in a concentration of 10% (V/V), followed by culturing at 37° C. for 5 hours. The starters of the thermophilus bacteria and the lactobacillus bacteria were inoculated in cow's milk, homogenized and then sterilized at 90° C. for 10 minutes, in ratios of the former to the latter starter of (1) 1.0:2.0, (2) 1.5:1.5, (3) 2.5:0.5, (4) 2.8:0.2 and (5) 5.9:0.1 in percentage by volume, and then the starter of the Bifidobacteria was further added to the every test composition of (1) to (5) in a concentration of 5.0% (V/V). Fermentation was carried out at 40° C. for 3.5–4.5 hours followed by immediate cooling to obtain the fermented milk samples having a pH of about 4.5. The numbers of viable cells of the thermophilus bacteria and the lactobacillus bacteria in these fermented milk samples and the ratios of the numbers of these two bacteria, along with changes in the number of viable cells and survival fraction of the Bifidobacteria and pH after being stored in 5° C. for 7 days, are shown in Table 2. Selective counting of the numbers of vaible cells of the thermophilus bacteria and the lactobacillus bacteria was possible from the differences in form of colonies on the agar plate of the nutrient medium containing Brom cresol purple. The number of viable cells of the Bifidobacteria was measured according to the colony formation in a MGLP agar column [Journal of Food Hygenic Society of Japan, volume 23, page 39 (1982)] which is a medium for selective colony formation in the Bifidobacteria after the decimal dilution of the fermented milk sample with Mitsuoka's dilutent solution for anaerobic bacteria ]Mitusoka: Rinshokensa (Journal of Medical Technology), Volume 18, page 1163 (1974)]. Survival fraction of the Bifidobacteria was given by percentage (%) of the number of viable cells after being stored for 7 days to the number of viable cells immediately after preparation.

The number of viable cells of the thermophilus bacteria and the lactobacillus bacteria in the fermented milk samples after being stored for 7 days were omitted because they were on the equivalent level with those values immediately after preparation.

manner as described in the above section (4). The survival fractions of the Bifidobacteria, when the number of viable cells of the thermophilus bacteria was about 40 times that of the lactobacillus bacteria and the fermented milk samples were stored at 5° C. for 7 days, exceeded 10% in the case of using the S bacteria, whereas the survival fractions were all lower than 1% in the case where the thermophilus bacteria having a low oxygen uptaking ability, and the standard 9Y and ATCC 19258 were employed under the same conditions. The S bacteria is concluded to effect a remarkably high survival on the Bifidobacteria.

(6) Effect of the thermophilus bacteria on the survival on various Bifidobacteria:

The following tests were conducted to estimate the activities of the thermophilus bacteria on the survival of various well known Bifidobacteria in fermented milk. Four strains of the Bifidobacteria, *Bifidobacterium bifidum* ATCC 15696, *Bifidobacterium infantis* ATCC

TABLE 2

| St | No. | Starter added | | | Immediately after preparation | | | | | 7 days after preparation | | Survival fraction (%) |
|---|---|---|---|---|---|---|---|---|---|---|---|---|
| | | St | L | B | pH | St Number | L Number | Ratio | B Number | pH | B Number | |
| STH - 32 | 1 | 1.0 | 2.0 | 5.0 | 4.51 | $4.1 \times 10^8$ | $3.8 \times 10^8$ | 1.1 | $1.5 \times 10^8$ | 4.37 | $5.1 \times 10^3$ | $3.4 \times 10^{-3}$ |
| | 2 | 1.5 | 1.5 | 5.0 | 4.50 | $5.5 \times 10^8$ | $1.8 \times 10^8$ | 3.1 | $1.7 \times 10^8$ | 4.38 | $2.0 \times 10^4$ | $1.2 \times 10^{-2}$ |
| | 3 | 2.5 | 0.5 | 5.0 | 4.53 | $6.4 \times 10^8$ | $4.9 \times 10^7$ | 13.1 | $1.6 \times 10^8$ | 4.40 | $8.2 \times 10^4$ | $5.1 \times 10^{-2}$ |
| | 4 | 2.8 | 0.2 | 5.0 | 4.55 | $9.1 \times 10^8$ | $3.0 \times 10^7$ | 30.3 | $1.6 \times 10^8$ | 4.40 | $2.6 \times 10^5$ | $1.6 \times 10^{-1}$ |
| | 5 | 5.9 | 0.1 | 5.0 | 4.55 | $1.1 \times 10^8$ | $2.3 \times 10^7$ | 47.8 | $2.0 \times 10^8$ | 4.47 | $1.3 \times 10^6$ | $6.5 \times 10^{-1}$ |
| M - 8205 | 1 | 1.0 | 2.0 | 5.0 | 4.50 | $3.8 \times 10^8$ | $3.9 \times 10^8$ | 0.97 | $1.6 \times 10^8$ | 4.38 | $1.5 \times 10^6$ | 0.94 |
| | 2 | 1.5 | 1.5 | 5.0 | 4.50 | $6.2 \times 10^8$ | $1.7 \times 10^8$ | 3.6 | $1.9 \times 10^8$ | 4.41 | $2.8 \times 10^6$ | 1.5 |
| | 3 | 2.5 | 0.5 | 5.0 | 4.52 | $6.5 \times 10^8$ | $6.7 \times 10^7$ | 9.7 | $1.9 \times 10^8$ | 4.44 | $1.1 \times 10^7$ | 5.8 |
| | 4 | 2.8 | 0.2 | 5.0 | 4.55 | $9.8 \times 10^8$ | $5.0 \times 10^7$ | 19.6 | $2.1 \times 10^8$ | 4.45 | $2.3 \times 10^7$ | 11.0 |
| | 5 | 5.9 | 0.1 | 5.0 | 4.55 | $1.1 \times 10^9$ | $2.5 \times 10^7$ | 44.0 | $2.2 \times 10^8$ | 4.50 | $4.5 \times 10^7$ | 20.5 |

Note:
St: thermophilus bacteria
B: Bifidobacteria
L: lactobacillus bacteria
Number: per 1 g
Ratio: ratio of viable cell number of St to that of L
Starter added: % (V/V)

As is obvious from Table 2, the survival fraction of the Bifidobacteria, after being stored, is an increased with increase in the ratio of the number of viable cells of STH-50 to those of the lactobacillus bacteria immediately after the termination of culturing. It is higher by 30–100 times, when compared to the case that the ratio of the number of bacteria is 0.5.

On the contrary, in the case of STH-32 having a low oxygen uptake ability, the survival fraction of the Bifidobacteria after being stored is low even under the same conditions as those for the S bacteria. Significant survival survival of the Bifidobacteria, after being strored, is by no means ensured by employing STH-32, the thermophilus bacteria for fermented milk.

(5) Effect of the S bacteria upon the survival ratio of the Bifidobacteria:

The present inventors tested the survivals of the Bifidobacteria when fermented milk samples are prepared with S bacteria except M-8205, thermophilus bacteria having a low oxygen uptake ability except STH-32, standard 9Y and ATCC 19258 in the same 15697, *Bifidobacterium breve* ATCC 15700 and *Bifidobacterium adolescentis* ATCC 15706, and the thermophilus bacteria, ATCC 19258 and M-8205 were subjected to the tests.

Starters of the thermophilus bacteria, the lactobacillus bacteria and the Bifidobacteria prepared in the same manner as described in the foregoing section (4) were inoculated to the separate milk media, homogenized and sterilized at 90° C. for 10 minutes, in concentrations of 2.8% (V/V), 0.2%(V/V) and 1.5% (V/V), respectively. Fermentation was carreid out at 40° C. for about 4 hours, followed by immediate cooling to prepare fermented milk samples having a pH of 4.6. Changes in the number of viable cells of the Bifidobacteria, survival fractions when the fermented milk samples were stored at 5° C. for 7 days, and pH are shown in Table 3.

The ratio of the number of viable cells of the thermophilus bacteria to that of the lactobacillus bacteria in the fermented milk samples was about 30 in the case of the ATCC 19258 strain, and about 20 in the case of the M-8205 strain.

TABLE 3

| Thermophilus bacteria used | Bifidobacterium used | Immediately after preparation | | 7 days after preparation | | |
|---|---|---|---|---|---|---|
| | | pH | Number of viable cells (per g) | pH | Number of viable cells (per g) | Survival ratio (%) |
| ATCC 19258 | *Bifidobacterium bifidum* ATCC 15696 | 4.60 | $6.6 \times 10^7$ | 4.48 | $4.0 \times 10$ | $6.1 \times 10^{-5}$ |
| | *Bifidobacterium infantis* 15697 | 4.58 | $1.2 \times 10^8$ | 4.30 | $1.4 \times 10^4$ | $1.2 \times 10^{-2}$ |

TABLE 3-continued

| Thermophilus bacteria used | Bifidobacterium used | Immediately after preparation | | 7 days after preparation | | |
|---|---|---|---|---|---|---|
| | | pH | Number of viable cells (per g) | pH | Number of viable cells (per g) | Survival ratio (%) |
| M - 8205 | Bifidobacterium bruve ATCC 15700 | 4.61 | $1.4 \times 10^8$ | 4.50 | $2.2 \times 10^3$ | $1.6 \times 10^{-3}$ |
| | Bifidobacterium adolescentis ATCC 15706 | 4.59 | $4.0 \times 10^6$ | 4.42 | $3.2 \times 10^2$ | $8.0 \times 10^{-3}$ |
| | Bifidobacterium bifidum ATCC 15696 | 4.59 | $6.2 \times 10^7$ | 4.50 | $3.6 \times 10^6$ | 5.8 |
| | Bifidobacterium infantis ATCC 15697 | 4.55 | $7.5 \times 10^7$ | 4.47 | $7.9 \times 10^6$ | 10.5 |
| | Bifidobacterium breve ATCC 15700 | 4.65 | $1.3 \times 10^8$ | 4.54 | $6.5 \times 10^6$ | 5.0 |
| | Bifidobacterium adolescentis ATCC 15706 | 4.58 | $2.4 \times 10^7$ | 4.44 | $2.7 \times 10^6$ | 11.3 |

It is evident from Table 3 that the survival fraction of the Bifidobacteria in fermented milk varies dependent on the Bifidobacteria species, but is about 800–100,000 times as high in the case of using the M-8205 strain of the S bacteria as that in the case of using the ATCC 19258 strain. The S bacteria remarkably effects the stimulation of survival of various well known Bifidobacteria due to the protective activity on the Bifidobacteria.

When fermented milk products containing the S bacteria and the Bifidobacteria were prepared with *Lactobacillus acidophilus*, *Lactobacillus helveticus*, *Lactobacillus jugurti* or *Lactobacillus casei*, which are taxonomically related to *Lactobacillus bulgaricus*, the survival fraction of the Bifidobacteria was also ensured by designing the number of viable cells of the S bacteria to be higher than 10 times that of the lactobacillus bacteria.

EXAMPLE 1

A subculture of *Streptococcus thermophilus* M-8202 (STH-01) was inoculated in 2500 ml of 10% (W/W) reconstituted skim milk, sterilized at 90° C. for 30 minutes and cooled, in a concentration of 3% (V/V), and was cultured at 37° C. for 16 hours. Separately, a subculture of *Lactobacillus bulgaricus* ATCC 11842 was inoculated in 100 ml of a medium of the same composition as above, sterilized at 115° C. for 15 minutes and cooled, in a concentration of 3% (V/V), and was cultured at 37° C. for 16 hours.

A subculture of *Bifidobacterium longum* ATCC 15708 was inoculated in 1500 ml of a culture medium containing 0.2% (W/W) of yeast extract and 10% (W/W) of skim milk powder, which was sterilized at 90° C. for 30 minutes, in a concentration of 10% (V/V), and was cultured at 37° C. for 6 hours.

Separately, 100 l of milk, in which the concentrations of milk fat and non-fat milk solid were adjusted to 3.1% (W/W) and 9.0% (W/W) respectively, was heated to 60° C., homogenized under a pressure of 150 kg/cm², sterilized at 90° C. for 10 minutes and cooled to 40° C.

The sterilized milk was inoculated with the three starters and was dispensed in containers of 500 ml capacity, sealed, fermented at 40° C. for 4 hours and immediately chilled. The fermented milk, thus obtained, had an acidity of 0.78% as expressed by lactic acid concentration and contained $110 \times 10^7$/ml of *Streptococcus thermophilus*, $75 \times 10^6$/ml of *Lactobacillus bulgaricus* and $90 \times 10^6$/ml of *Bifidobacterium longum*. The number of viable cells of *Bifidobacterium longum* in the fermented milk, after being stored at 5° C for 7 days, was $12 \times 10^6$/ml and the survival fraction was 13.3%.

EXAMPLE 2

*Streptococcus thermophilus* M-8204 (STH-23) was inoculated in 30 l of 18% (W/W) reconstituted skim milk containing 0.1% (W/W) of casamino acid, which was sterilized at 90° C. for 30 minutes and cooled at 39° C., in a concentration of 3% (V/V), and was subjected to fermentation at 37°–38° C. for 18 hours. *Lactobacillus acidophilus* ATCC 4356 was inoculated in 2 l of a culture medium containing 0.1% (W/W) of yeast extract and 10% (W/W) of skim milk powder, which was sterilized at 115° C. for 15 minutes and cooled, in a concentration of 3% (V/V), and subjected to fermentation at 37° C. for 18 hours.

*Bifidobacterium infantis* ATCC 15697 was inoculated in 10 l of a culture medium containing 0.1% (W/W) of casamino acid, 0.1% (W/W) of yeast extract and 12% (W/W) of skim milk powder, which was sterilized at 90° C. for 30 minutes and cooled, and was subjected to fermentation at 37° C. for 8 hours.

Separately, 65 kg of syrup containing 13 kg of sugar, 0.6 kg of acid-resistant carboxy methyl cellulose and 0.2 kg of flavoring agent was sterilized at 120° C. for 2 seconds and cooled to about 20° C. Thirty kg of the fermented milk by *Streptococcus thermophilus*, 2 kg of the fermented milk by *Lactobacillus acidophilus*, and 10 kg of the fermented milk by *Bifidobacterium infantis* were mixed with 58 kg of the syrup. The mixture was twice homogenized at of 50 kg/cm² and 100 kg/cm², and filled in glass bottles of 200 ml of a volume to produce about 400 bottles of fermented milk beverage. The thus obtained fermented milk beverage of pH 4.8 contained $32 \times 10^7$/ml of *Streptococcus thermophilus*, $22 \times 10^6$/ml of *Lactobacillus acidophilus*, $27 \times 10^7$/ml of *Bifidobacterium infantis*, and an acidity of 0.63% as expressed by lactic acid concentration. The number of viable cells of *Bifidobacterium infantis* in the beverage after being stored at 5° C. for 7 days was $29 \times 10^6$/ml and the survival fraction was 10.7%.

What is claimed is:

1. A culture containing a viable cell mass of Bifidobacteria and lactic acid bacteria, which is obtained by incubating microorganisms of the genus Bifidobacterium, the genus Lactobacillus, and the species *Streptococcus thermophilus* in a medium containing milk as a main ingredient said culture immediately after incubating comprising:

(a) at least $1 \times 10^8$ cells per milliliter of the culture of *Streptococcus thermophilus* selected from the group consisting of *Streptococcus thermophilus* M-8202 (FERM BP-351), M-8203 (FERM BP-352), M-8204 (FERM BP-353), and M-8205 (FERM BP- 354) and mixtures thereof having an oxygen uptake ability of at least 30 nano moles per milligram of dried cells of said *Streptococcus thermophilus* per minute as defined by the oxygen consumption which is determined according to Warbur's manometric method, (b) at least $2 \times 10^7$ cells per milliliter of the culture of the genue Bifidobacterium and at least a 5% survival of the cells of the genus Bifidobacterium as expressed by the ratio in percent of the number of cells after storage at 5° C. for 7 days to the number of cells prior to storage, and (c) at least $5 \times 10^6$ cells per milliliter of the culture of the genus Lactobacillus, and the viable cells of said *Streptococcus thermophilus* being at least 10 times that of the number of viable cells of the genus Lactobacillus.

2. A process for preparing a culture containing a viable cell mass of Bifidobacterium and lactic acid bacteria, comprising the steps of:

(a) inoculating a mixture which is composed of microoganisms of the genus Bifidobacterium, the genus Lactobacillus, and the species *Streptococcus thermophilus* in the respective ratios by weight of 100:0.5 to 50:3.0 to 600 in a medium contaiing milk as a main ingredient, said *Streptococcus thermophilus* being selected from the group consisting of *Streptococcus thermophilus* M-8202 (FERM BP-351), M-8203 (FERM BP-352), M-8304 (FERM BP-353), and M-8205 (FERM BP-354), said *Streptococcus thermophilus* having an oxygen uptake ability of at least 30 nano mole per milligram of dried cells of said *Streptococcus thermophilus* per minute as defined by the oxygen consumption which is determined according to Warburg's manometric method, and (b) aerobically incubating the medium.

3. A process according to claim 2, wherein the incubation is carried out at 37° to 42° C. for 3 to 24 hours.

4. A process for preparing a culture containing a viable cell mass of Bifidobacterium and lactic acid bacteria, comprising the steps of:

(a) separately inoculating a microorganism of the genus Bifidobacterium, the genus Lactobacillus, and the species *Streptococcus thermophilus in a respective medium containing milk as a main ingredient*, said *Streptococcus thermophilus* being selected from the group consisting of *Streptococcus thermophilus* M-8202 (FERM BP-351), M-8203 (FERM PB-352), M-8204 (FERM BP-353) and M-8205 (FERM BP-354), said *Streptococcus thermophilus* having an oxygen uptake ability of at least 30 nano mole per milligram of dried cells of said *Streptococcus thermophilus* per minute as defined by the oxygen consumption which is determined according to Warburg's manometric method, (b) aerobically incubating each medium to obtain an incubated material, and (c) mixing together the incubated material obtained from the genus Bifidobacterium, the incubated material obtained from the genus Lactobacillus, and the incubated material obtained from the species *Streptococcus thermophilus* in the respective ratio by weight of 100:0.28 to 625: and 11 to 24,800.

5. A process according to claim 4, wherein the incubation is carried out at 37° to 42° C. for 3 to 24 hours.

* * * * *